United States Patent
Yamazaki et al.

(10) Patent No.: US 9,974,754 B2
(45) Date of Patent: May 22, 2018

(54) HYDROUS ADHESIVE PATCH

(71) Applicants: MARUISHI PHARMACEUTICAL CO., LTD., Osaka-shi (JP); KYUKYU PHARMACEUTICAL CO., LTD., Chuo-ku (JP)

(72) Inventors: Yuhiro Yamazaki, Imizu (JP); Nobuhiro Nosaka, Imizu (JP)

(73) Assignees: MARUISHI PHARMACEUTICAL CO., LTD., Osaka-shi (JP); KYUKYU PHARMACEUTICAL CO., LTD., Chuo-ku (JP)

( * ) Notice: Subject to any disclaimer, the term of this patent is extended or adjusted under 35 U.S.C. 154(b) by 72 days.

(21) Appl. No.: 15/102,605

(22) PCT Filed: Dec. 17, 2014

(86) PCT No.: PCT/JP2014/083335
§ 371 (c)(1),
(2) Date: Jun. 8, 2016

(87) PCT Pub. No.: WO2015/093503
PCT Pub. Date: Jun. 25, 2015

(65) Prior Publication Data
US 2016/0310441 A1  Oct. 27, 2016

(30) Foreign Application Priority Data

Dec. 18, 2013 (JP) ................................. 2013-261118

(51) Int. Cl.
| A61K 9/70 | (2006.01) |
| A61K 47/10 | (2017.01) |
| A61K 47/14 | (2017.01) |
| A61K 31/4174 | (2006.01) |
| A61F 13/00 | (2006.01) |
| A61F 13/02 | (2006.01) |

(52) U.S. Cl.
CPC ...... *A61K 9/7061* (2013.01); *A61F 13/00063* (2013.01); *A61F 13/0253* (2013.01); *A61K 9/7069* (2013.01); *A61K 31/4174* (2013.01); *A61K 47/10* (2013.01); *A61K 47/14* (2013.01)

(58) Field of Classification Search
None
See application file for complete search history.

(56) References Cited

U.S. PATENT DOCUMENTS

| 4,978,531 | A | * | 12/1990 | Yamazaki | ............ A61K 9/7053 |
| | | | | | 424/448 |
| 5,124,157 | A | | 6/1992 | Colley et al. | |
| 5,176,916 | A | | 1/1993 | Yamanaka et al. | |
| 5,217,718 | A | * | 6/1993 | Colley | ............ A61K 9/703 |
| | | | | | 424/448 |
| 5,352,456 | A | | 10/1994 | Fallon et al. | |
| 5,438,067 | A | | 8/1995 | Jalonen et al. | |
| 5,817,332 | A | | 10/1998 | Urtti et al. | |
| 5,820,875 | A | | 10/1998 | Fallon et al. | |
| 6,761,900 | B2 | * | 7/2004 | Shudo | ............ A61K 9/7061 |
| | | | | | 424/443 |
| 7,001,609 | B1 | | 2/2006 | Matson et al. | |
| 7,018,647 | B1 | * | 3/2006 | Yamasaki | ............ A61K 9/7061 |
| | | | | | 424/443 |
| 2010/0068248 | A1 | * | 3/2010 | Funakoshi | ............ A61L 15/585 |
| | | | | | 424/448 |

FOREIGN PATENT DOCUMENTS

| JP | 60-163811 A | 8/1985 |
| JP | 4-1127 A | 1/1992 |
| JP | 5-503916 A | 6/1993 |
| JP | 3011459 B2 | 2/2000 |
| JP | 3043064 B2 | 5/2000 |
| JP | 3483881 B2 | 1/2004 |
| JP | 3734267 B2 | 1/2006 |
| WO | 91/02505 A1 | 3/1991 |
| WO | WO 2015/054059 A2 | 4/2015 |

OTHER PUBLICATIONS

International Search Report dated Mar. 31, 2015 in PCT/JP2014/083335, filed Dec. 17, 2014.
Extended European Search Report dated Jun. 21, 2017 in Patent Application No. 14872467.7.

* cited by examiner

*Primary Examiner* — Robert A Wax
*Assistant Examiner* — Quanglong N Truong
(74) *Attorney, Agent, or Firm* — Oblon, McClelland, Maier & Neustadt, L.L.P.

(57) ABSTRACT

Provided is a patch providing sufficiently high absorbability of dexmedetomidine and less skin irritation.

Hydrous adhesive patch comprising dexmedetomidine or a salt thereof and a water-soluble polymer.

21 Claims, No Drawings

HYDROUS ADHESIVE PATCH

TECHNICAL FIELD

The present invention relates to a patch containing dexmedetomidine or a salt thereof useful as a sedative.

BACKGROUND ART

Dexmedetomidine or a salt thereof, which is an agonist of $\alpha_2$ adrenergic receptor, has a sedative action, an analgesic action and a sympathoinhibitory action, and is used as a sedative. At present, dexmedetomidine or a salt thereof is used in Japan for sedation during artificial respiration in intensive care and after removing artificial respirators; whereas, in foreign countries, it is widely used as a sedative and an analgesic. As the dosage form of dexmedetomidine, intravenous administration alone is used.

As another dosage form of dexmedetomidine, a transdermal preparation is investigated. As examples, a non-aqueous patch composed of a backing layer/anchor adhesive layer/porous intermediate layer/contact adhesive layer/release liner (Patent Document 1); a reservoir patch (Patent Document 2); a patch using a cyclodextrin derivative (Patent Document 3); and a patch containing a carboxylic acid salt of dexmedetomidine (Patent Document 4) have been reported.

CITATION LIST

Patent Document

[Patent Document 1] JP-B-3043064
[Patent Document 2] JP-B-3011459
[Patent Document 3] JP-B-3734267
[Patent Document 4] JP-B-3483881

SUMMARY OF THE INVENTION

Problem to be Solved by the Invention

These conventional dexmedetomidine-containing patches, however, employ a complicated preparation structure and release mechanism or employ a specific salt of dexmedetomidine in order to obtain high absorbability. Because of this, troubles such as skin irritation and rash have been more likely to occur. Accordingly, an object of the present invention is to provide a patch providing sufficiently high absorbability of dexmedetomidine and less skin irritation.

Means for Solving the Problem

Thus, the present inventors produced dexmedetomidine-containing patches using various base agents and checked transdermal absorbability thereof. They surprisingly found that a water-rich hydrous adhesive patch produced by blending dexmedetomidine or a salt thereof and a water-soluble polymer provides excellent transdermal absorbability of dexmedetomidine and less skin irritation. Based on the finding, the present invention was accomplished.

More specifically, the present invention provides the following [1] to [8].

[1] A hydrous adhesive patch comprising dexmedetomidine or a salt thereof and a water-soluble polymer.

[2] The hydrous adhesive patch according to [1], wherein a content of the water-soluble polymer in an adhesive gel base is 5 to 25 mass % and the content of water in the adhesive gel base is 25 to 70 mass %.

[3] The hydrous adhesive patch according to [1] or [2], wherein the water-soluble polymer comprises a polyacrylic acid or a salt thereof and carboxymethylcellulose or a salt thereof.

[4] The hydrous adhesive patch according to any of [1] to [3], wherein the adhesive gel base has a pH of 6 to 7.

[5] The hydrous adhesive patch according to any of [1] to [4], further comprising one or more selected from a polyhydric alcohol and a fatty acid ester-based absorption enhancer.

[6] The hydrous adhesive patch according to any of [1] to [4], further comprising one or more selected from a polyhydric alcohol, a higher fatty acid alkyl ester, a dibasic acid dialkyl ester and a polyhydric alcohol fatty acid ester.

[7] The hydrous adhesive patch according to any of [1] to [4], further comprising one or more selected from propylene glycol, glycerin, a sugar alcohol, isopropyl myristate and propylene glycol monocaprylate.

[8] The hydrous adhesive patch according to any of [1] to [7], wherein the patch is a sedative.

Advantageous Effects of the Invention

The patch of the present invention provides excellent transdermal absorbability of dexmedetomidine and less skin irritation. Thus, the effect of dexmedetomidine as a sedative can be stably obtained for a long time.

EMBODIMENTS FOR CARRYING OUT THE INVENTION

The active ingredient of the patch according to the present invention is dexmedetomidine or a salt thereof. Dexmedetomidine, the chemical name of which is (+)-(S)-4-[1-(2,3-dimethylphenyl)ethyl]-1H-imidazole, is an agonist of a central $\alpha_2$ adrenergic receptor. Examples of a salt of dexmedetomidine include an acid addition salt inorganic acid addition salt such as hydrochloride, sulfate, nitrate and phosphate is preferable, and in particular, a hydrochloride is preferable.

The content of dexmedetomidine or a salt thereof in the adhesive gel base of the patch is preferably 0.1 to 10 mass %, more preferably 0.1 to 7 mass %, in view of transdermal absorbability, skin irritation and stability of a preparation.

Examples of the water-soluble polymer to be used in the patch of the present invention include natural water-soluble polymers such as gelatin, starch and agar; water-soluble cellulose derivatives such as carboxymethylcellulose or a salt thereof, hydroxypropylcellulose, hydroxypropylmethylcellulose, methylcellulose and ethylcellulose; processed starch such as acrylate starch; and synthetic water-soluble polymers such as a polyacrylic acid, a polyacrylate, a partially neutralized polyacrylic acid, a crosslinked polyacrylic acid, a carboxyvinyl polymer, a polyvinyl alcohol and a N-vinylacetamide-sodium polyacrylate copolymer. Among them, gelatin, a polyacrylic acid, a polyacrylate, partially neutralized polyacrylic acid, a crosslinked polyacrylic acid, a carboxyvinyl polymer, carboxymethylcellulose or a salt thereof, hydroxypropylcellulose and hydroxypropylmethylcellulose are preferable. These water-soluble polymers can be used singly or in combination of two or more.

Among these water-soluble polymers, a polyacrylic acid or a salt thereof and carboxymethylcellulose or a salt thereof are further preferably used in combination in view of transdermal absorbability of dexmedetomidine or a salt thereof, skin irritation and stability of a preparation. Among the polyacrylic acids or salts thereof and carboxymethylcellulose or salts thereof, a combination of a partially neutralized polyacrylic acid, a sodium polyacrylate and sodium carboxymethylcellulose is more preferable. Herein the mass ratio of the content of a polyacrylic acid or a salt thereof (PA) to the content of carboxymethylcellulose or a salt thereof (CMC), i.e., the ratio (PA:CMC), is preferably 1:5 to 5:1, more preferably 1:3 to 3:1, even more preferably 1:2 to 2:1. When a partially neutralized polyacrylic acid (PA), sodium polyacrylate (PANa) and sodium carboxymethylcellulose (CMCNa) are used, the mass ratio of the contents thereof (PA+PANa):(CMCNa) is preferably 1:5 to 5:1, more preferably 1:3 to 3:1, more preferably 1:2 to 2:1.

The content of the water-soluble polymer in the adhesive gel base of the patch is preferably 5 to 25 mass %, more preferably 5 to 20 mass % in view of transdermal absorbability, skin irritation and stability of a preparation.

The patch of the present invention is a hydrous adhesive patch. In view of the transdermal absorbability of dexmedetomidine or a salt thereof and skin irritation, it is important that the patch contains relatively a large amount of water. The content of water in the adhesive gel base of the patch is preferably 25 to 70 mass %, more preferably 30 to 60 mass %, more preferably 30 to 55 mass % in view of transdermal absorbability, skin irritation and stability of a preparation.

The patch of the present invention preferably contains one or two or more selected from a polyhydric alcohol and a fatty acid ester-based absorption enhancer in view of improving transdermal absorbability of dexmedetomidine or a salt thereof.

Examples of the polyhydric alcohol include glycols such as ethylene glycol, propylene glycol, dipropylene glycol, 1,3-butylene glycol, polyethylene glycol (molecular weight: 1000 or less) and polypropylene glycol (molecular weight: 1000 or less); glycerins such as glycerin, diglycerin and polyglycerin; and sugar alcohols such as sorbitol and maltitol. These polyhydric alcohols can be used singly or in combination of two or more. Among them, propylene glycol, a glycerin and a sugar alcohol are preferable. Particularly, propylene glycol is preferably added in order to prevent crystallization of dexmedetomidine or a salt thereof in the adhesive gel base. Note that, as described later, even if dexmedetomidine or a salt thereof is crystallized in a preparation, it does not influence on skin permeability much; however, a crystal is preferably not present in view of appearance of a preparation.

The content of the polyhydric alcohol in the adhesive gel base of the patch is preferably 10 to 60 mass %, more preferably 20 to 55 mass %, more preferably 25 to 55 mass % in view of transdermal absorbability and skin irritation.

Examples of the fatty acid ester-based absorption enhancer include higher fatty acid alkyl esters (preferably a $C_8$-$C_{24}$ fatty acid $C_1$-$C_6$ alkyl ester) such as isopropyl myristate, isopropyl palmitate, butyl stearate and butyl myristate; dibasic fatty acid dialkyl esters (preferably, a dibasic acid di-$C_1$-$C_6$ alkyl ester) such as diisopropyl sebacate, diethyl sebacate and diisopropyl adipate; and polyhydric alcohol fatty acid esters (preferably, a polyhydric alcohol $C_8$-$C_{24}$ fatty acid ester) such as propylene glycol monocaprylate, propylene glycol dicaprylate, propylene glycol dicaprate, glyceryl monocaprylate, tetraglyceryl monocaprylate and sorbitan hexacaprylate.

Among them, a higher fatty acid alkyl ester, a polyhydric alcohol fatty acid ester and a dibasic fatty acid dialkyl ester are preferable, particularly, a higher fatty acid alkyl ester and a polyhydric alcohol fatty acid ester are more preferable, and further, isopropyl myristate and propylene glycol monocaprylate are even more preferable since a desired analgesic level can be easily maintained in addition to a high absorption enhancing effect.

Although these fatty acid ester-based absorption enhancers may not be added, they are contained in the adhesive gel base of the patch in an amount of preferably 0.01 to 15 mass %, more preferably, 0.1 to 10 mass %, more preferably 0.1 to 5 mass %.

Among these polyhydric alcohols and the absorption enhancers, one or more selected from propylene glycol, glycerin, a sugar alcohol, a higher fatty acid alkyl ester and a polyhydric alcohol fatty acid ester are preferably used in combination; and one or more selected from propylene glycol, glycerin, a sugar alcohol, isopropyl myristate and propylene glycol monocaprylate are preferably used in combination.

More specifically, glycerin and a sugar alcohol are preferably used in combination; further, glycerin, a sugar alcohol and a higher fatty acid alkyl ester are more preferably used in combination; further, glycerin, a sugar alcohol, a higher fatty acid alkyl ester and propylene glycol are even more preferably used in combination; and further, glycerin, a sugar alcohol, a higher fatty acid alkyl ester, a polyhydric alcohol fatty acid ester and propylene glycol are even more preferably used in combination. Herein, the sugar alcohol is particularly preferably sorbitol. Furthermore, the higher fatty acid alkyl ester is particularly preferably isopropyl myristate. The polyhydric alcohol fatty acid ester is particularly preferably propylene glycol monocaprylate. If a polyhydric alcohol fatty acid ester is blended herein, the long-term storage stability of a patch is improved.

Note that other absorption enhancers can be blended in the patch of the present invention. Examples thereof include $C_8$ to $C_{18}$ fatty acids such as caprylic acid, capric acid, caproic acid, lauric acid, myristic acid, palmitic acid and stearic acid; $C_8$ to $C_{18}$ higher alcohols such as capryl alcohol, decanol, lauryl alcohol, myristyl alcohol, cetyl alcohol and oleyl alcohol; polyoxyethylene alkyl ethers, alkyl sulfates and N-methyl-2-pyrrolidone.

Other than the aforementioned components, a crosslinking agent, a pH adjuster, a chelating agent, a surfactant and other additives can be blended in the patch of the present invention.

The crosslinking agent is a component which crosslinks a water-soluble polymer to form gel, and is preferably aluminum compound. Examples of the aluminum compound include aluminum hydroxide, aluminum chloride, synthetic aluminum silicate, dried aluminum hydroxide gel, magnesium hydroxide-aluminium hydroxide, aluminum sulfate and dihydroxyaluminum aminoacetate.

The content of the crosslinking agent in the adhesive gel base of the patch is preferably 0.001 to 1 mass %, more preferably 0.01 to 1 mass % in view of transdermal absorbability and stability of a preparation.

As the pH adjuster, lactic acid, tartaric acid, citric acid, acetic acid and salts of these, etc. are used. The content of the pH adjuster in the adhesive gel base of the patch is preferably 0.001 to 1 mass, more preferably 0.01 to 1 mass %. The pH of the adhesive gel base of the hydrous adhesive patch is preferably adjusted to 6 to 7 in order to enhance transdermal absorbability of dexmedetomidine or a salt thereof.

Examples of the chelating agent include sodium edetate (EDTA), glucono delta lactone and sodium polyphosphates such as sodium metaphosphate. The content of the chelating agent in the adhesive gel base of the patch is 0.001 to 1 mass %, more preferably 0.01 to 1 mass %.

Examples of the surfactant include polyoxyethylene sorbitan fatty acid ester, sorbitan fatty acid ester, glycerin fatty acid ester, polyoxyethylene glycerin fatty acid ester, polyglycerin fatty acid ester, polyoxyethylene hydrogenated castor oil and polyoxyethylene alkyl ether. These surfactants may not be added and the content thereof in the adhesive gel base of the patch is preferably 0.01 to 5 mass %, more preferably 0.01 to 3 mass %.

Examples of other additives include an acrylic copolymer (a methacrylic acid-acrylic acid-n-butyl copolymer, a methyl acrylate-2-ethylhexylacrylate copolymer), an antiseptic agent, an antioxidant, a stabilizer, an excipient (kaolin, silicic anhydride, titanium oxide, talc, etc.), a fragrance, a colorant and an oil component (crotamiton, castor oil).

The hydrous adhesive patch of the present invention is generally produced by applying an adhesive gel base containing the aforementioned components onto a backing layer and attaching a covering film (release sheet) to the surface of the adhesive gel base.

As the backing layer, a water impermeable backing layer is preferable and a laminate obtained by laminating nonwoven cloth on a film formed of a polyolefin such as polyethylene terephthalate, polyethylene and polypropylene is preferable.

As the covering film, a polyolefin film such as a polyethylene film and a polypropylene film, and a polyester film are used. Furthermore, these films may be subjected to a treatment with silicon remover, a corona discharge treatment and an emboss treatment may be applied.

The amount of adhesive gel base applied is preferably 40 to 400 g/m$^2$, ore preferably 50 to 300 g/m$^2$.

The patch of the present invention is preferably formed into a shape such as square, circle and ellipse having a size of 10 to 100 cm$^2$.

Since the hydrous adhesive patch of the present invention is a patch, a predetermined amount of dexmedetomidine or a salt thereof can be conveniently administered without staining hands in applying it. Furthermore, since the hydrous adhesive patch of the present invention contains an effective amount of dexmedetomidine or a salt thereof, and provides less skin irritation and satisfactory transdermal absorbability, a continuous effect can be expected on consecutive days, a desired sedative level can be quickly obtained and a sedative action can be stably obtained by exchanging an old patch with a fresh patch 1 to 3 times per day even though an intravenous administration means is not taken.

Note that, the stable sedative action refers to an action providing a sedative level of score 0 to −2 when evaluation is made according to RASS (Richmond Agitation-Sedation Scale).

To quickly obtain a stable sedative effect, the transdermal absorption rate of the hydrous adhesive patch according to the present invention, which is evaluated by using skin excised out of a hairless mouse abdomen, is preferably 3.40 µg/cm$^2$/hr or more, more preferably 4.45 µg/cm$^2$/hr or more in terms of the skin permeation rate of dexmedetomidine hydrochloride. Furthermore, the transdermal absorption rate in humans is preferably 0.2 µg/kg/hr or more.

EXAMPLES

The present invention will be more specifically described by way of Examples below; however, the present invention is not limited to these Examples.

Examples 1 to 10

Hydrous adhesive patches were produced in accordance with the formulations shown in Table 1 to Table 3.

TABLE 1

| Name of component | Example 1 | Example 2 | Example 3 | Example 4 |
|---|---|---|---|---|
| Dexmedetomidine hydrochloride | 1.00 | 1.00 | 1.00 | 1.00 |
| Propylene glycol | | 3.00 | 6.00 | 10.00 |
| Concentrated glycerin | 36.00 | 33.00 | 30.00 | 26.00 |
| D-sorbitol solution | 5.00 | 5.00 | 5.00 | 5.00 |
| Gelatin | 3.00 | 3.00 | 3.00 | 3.00 |
| Partially neutralized polyacrylic acid | 2.50 | 2.50 | 2.50 | 2.50 |
| Sodium polyacrylate | 2.50 | 2.50 | 2.50 | 2.50 |
| CMC-Na | 5.00 | 5.00 | 5.00 | 5.00 |
| Dihydroxyaluminum aminoacetate | 0.50 | 0.50 | 0.50 | 0.50 |
| Tartaric acid | 0.20 | 0.20 | 0.20 | 0.20 |
| EDTA-2Na | 0.10 | 0.10 | 0.10 | 0.10 |
| Purified water | 44.20 | 44.20 | 44.20 | 44.20 |
| Total (parts by mass) | 100.00 | 100.00 | 100.00 | 100.00 |

TABLE 2

| Name of component | Example 5 | Example 6 | Example 7 | Example 8 |
|---|---|---|---|---|
| Dexmedetomidine hydrochloride | 1.00 | 1.00 | 1.00 | 1.00 |
| Propylene glycol | | | | 6.00 |
| Concentrated glycerin | 36.00 | 36.00 | 36.00 | 30.00 |
| D-sorbitol solution | 5.00 | 5.00 | 5.00 | 5.00 |
| Isopropyl myristate | 0.30 | 0.50 | 1.00 | 0.50 |
| Gelatin | 3.00 | 3.00 | 3.00 | 3.00 |
| Partially neutralized polyacrylic acid | 2.50 | 2.50 | 2.50 | 2.50 |
| Sodium polyacrylate | 2.50 | 2.50 | 2.50 | 2.50 |
| CMC-Na | 5.00 | 5.00 | 5.00 | 5.00 |
| Dihydroxyaluminum aminoacetate | 0.50 | 0.50 | 0.50 | 0.50 |
| Tartaric acid | 0.20 | 0.20 | 0.20 | 0.20 |
| EDTA-2Na | 0.10 | 0.10 | 0.10 | 0.10 |
| Polysorbate 80 | 0.50 | 0.50 | 0.50 | 0.50 |
| Purified water | 43.40 | 43.20 | 42.70 | 43.20 |
| Total (parts by mass) | 100.00 | 100.00 | 100.00 | 100.00 |

TABLE 3

| Name of component | Example 9 | Example 10 |
|---|---|---|
| Dexmedetomidine hydrochloride | 1.00 | 1.00 |
| Propylene glycol | | 6.00 |
| Concentrated glycerin | 35.50 | 29.50 |
| D-sorbitol solution | 5.00 | 5.00 |
| Isopropyl myristate | 0.50 | 0.50 |
| Propylene glycol monocaprylate | 0.50 | 0.50 |
| Gelatin | 3.00 | 3.00 |
| Partially neutralized polyacrylic acid | 2.50 | 2.50 |
| Sodium polyacrylate | 2.50 | 2.50 |
| CMC-Na | 5.00 | 5.00 |
| Dihydroxyaluminum aminoacetate | 0.50 | 0.50 |
| Tartaric acid | 0.20 | 0.20 |
| EDTA-2Na | 0.10 | 0.10 |
| Polysorbate 80 | 0.50 | 0.50 |
| Purified water | 43.20 | 43.20 |
| Total (parts by mass) | 100.00 | 100.00 |

(1) To purified water, gelatin, tartaric acid, sodium edetate and dexmedetomidine hydrochloride were added and dissolved. To this solution, a dispersion solution, which was separately prepared by adding a partially neutralized polyacrylic acid, a sodium polyacrylate, sodium carboxymethylcellulose (CMC-Na), dihydroxyaluminum aminoacetate and, if necessary, isopropyl myristate, polysorbate 80 and propylene glycol monocaprylate to a polyhydric alcohol, was added and stirred to prepare an adhesive gel base.

(2) The adhesive gel base was spread onto a backing layer such that the amount of adhesive gel base applied became 160 g/m$^2$ and the adhesive surface of the adhesive gel base was covered with a polyester film treated with a silicon remover. Thereafter, thus obtained preparation was cut into pieces of a predetermined size to obtain hydrous adhesive patches of dexmedetomidine.

(3) As the backing layer, a laminate prepared by laminating polyester nonwoven cloth on a polyester film was used.

Test Example 1 <Skin Permeability Test>

Test Method

Skin was excised out from the abdomen of a hairless mouse (7 weeks old, male) and attached to a horizontal diffusion cell provided with a water jacket. A predetermined patch was applied to the skin at the stratum corneum side; and a phosphate buffer (pH 6.8, 2.5 mL) was supplied into a chamber at the receiver side of the cell. The temperature of the cell was maintained constant by circulating warm water of 32° C. through the water jacket. While stirring the solution in the chamber at the receiver side by a stirrer, 0.5 mL of aliquots were taken with time from the solution of the chamber at the receiver side and used as sample solutions. Immediately after taking the solution from the chamber at the receiver side, a fresh phosphate buffer (0.5 mL) was supplied to make up for it. The amount of dexmedetomidine hydrochloride in each of the sample solutions was determined by high performance liquid chromatography (HPLC) and a cumulative amount of dexmedetomidine hydrochloride permeated from the preparation into the solution in the chamber at the receiver side was obtained. Furthermore, based on the change in the cumulative amount of dexmedetomidine hydrochloride permeated with time, the permeation rate of dexmedetomidine hydrochloride at 6th hour to 9th hour after initiation of the test was calculated. The results are shown in Table 4 to Table 6.

In Table 4 to Table 6, the pH value of each preparation was also shown. The pH of each preparation was obtained by dissolving 1 part by mass of an adhesive gel base in purified water (9 parts by mass) by warming, and by measuring the pH of the solution by a pH meter after the temperature of the solution reached 20 to 25° C.

TABLE 4

Cumulative permeated amount and permeation rate of dexmedetomidine hydrochloride

| Cumulative permeated amount (µg/cm$^2$) | Example 1 | Example 2 | Example 3 | Example 4 |
|---|---|---|---|---|
| 3rd hour | 2.95 | 2.47 | 4.07 | 4.77 |
| 6th hour | 12.35 | 10.38 | 15.72 | 15.65 |
| 9th hour | 24.46 | 20.08 | 29.92 | 30.88 |
| Permeation rate (µg/cm$^2$/h) | 4.04 | 3.47 | 4.74 | 4.74 |
| pH of preparation | 6.6 | 6.5 | 6.6 | 6.5 |

TABLE 5

Cumulative permeated amount and permeation rate of dexmedetomidine hydrochloride

| Cumulative permeated amount (µg/cm$^2$) | Example 5 | Example 6 | Example 7 | Example 8 |
|---|---|---|---|---|
| 3rd hour | 4.73 | 8.80 | 6.87 | 6.97 |
| 6th hour | 16.92 | 28.77 | 24.99 | 24.49 |
| 9th hour | 33.93 | 53.44 | 48.74 | 43.34 |
| Permeation rate (µg/cm$^2$/h) | 5.67 | 8.22 | 7.91 | 6.28 |
| pH of preparation | 6.6 | 6.7 | 6.6 | 6.6 |

TABLE 6

Cumulative permeated amount and permeation rate of dexmedetomidine hydrochloride

| Cumulative permeated amount (µg/cm$^2$) | Example 9 | Example 10 |
|---|---|---|
| 3rd hour | 6.38 | 11.81 |
| 6th hour | 18.13 | 34.83 |
| 9th hour | 33.44 | 55.86 |
| Permeation rate (µg/cm$^2$/h) | 5.11 | 7.01 |
| pH of preparation | 6.6 | 6.7 |

From the results of Table 4 to Table 6, it was found that transdermal absorbability of dexmedetomidine or a salt thereof becomes satisfactory by blending it with a water-soluble polymer to prepare a water-rich hydrous adhesive patch. In addition, it was also found that the transdermal absorbability of dexmedetomidine or a salt thereof is improved by blending it with a polyhydric alcohol (propylene glycol, glycerin, sorbitol) or/and a higher fatty acid alkyl ester (isopropyl myristate). Note that it was also confirmed that the patches of Examples 1 to 10 were stable without skin irritation.

Test Example 2 <Skin Permeation Rate and Long-Term Stability>

The hydrous adhesive patches of Examples 1, 6, 8, 9 and 10 were produced and evaluated for long-term storage stability (presence or absence of crystal precipitation and stability of dexmedetomidine hydrochloride). Furthermore, the hydrous adhesive patch of Example 1 was also subjected to a skin permeability test after long-time storage in the same manner as in Test Example 1.

(Method for Confirming Crystal)

A preparation (10 cm$^2$) was packaged in an aluminum bag and stored at room temperature for 8 months. Thereafter, the presence or absence of a crystal of dexmedetomidine hydrochloride in the preparation was visually confirmed and evaluated in accordance with the following scores.

TABLE 7

| Score | Determination criteria |
|---|---|
| AA | Crystal is absent. |
| A | One to three extremely small crystals (diameter: about 1 mm) are present. |
| B | Crystals are present overall. |

(Stability Test of Dexmedetomidine Hydrochloride)

A preparation (10 cm$^2$, 160 mg in terms of dexmedetomidine hydrochloride) was packaged in an aluminum bag and stored at 60° C. for 3 weeks. After storage, dexmedetomidine hydrochloride contained in the preparation was extracted with methanol by heating under reflux. The amount of dexmedetomidine hydrochloride in the extract was determined by high performance liquid chromatography (HPLC) and a residual ratio (%) of dexmedetomidine hydrochloride after storage to an initial value was obtained.

TABLE 8

Stability improving effect by polyhydric alcohol fatty acid ester

|  | Example 1 | Example 6 | Example 8 | Example 9 | Example 10 |
|---|---|---|---|---|---|
| Presence or absence of crystal | B | B | AA | A | AA |
| Residual ratio (%) | 88.1 | 92.9 | 94.3 | 94.8 | 96.2 |

TABLE 9

Effect of dexmedetomidine hydrochloride crystallization on skin permeability

| Cumulative permeated | Example 1 | |
|---|---|---|
| amount (μg/cm$^2$) | Initial | Room temperature 8 M |
| 3rd hour | 2.95 | 4.81 |
| 6th hour | 12.35 | 15.51 |
| 9th hour | 24.46 | 26.98 |
| Permeation rate (μg/cm$^2$/h) | 4.04 | 3.82 |
| Presence or absence of crystal | AA | B |

From Table 8, it was found that even if dexmedetomidine hydrochloride is stored for a long time, the stability thereof is improved without precipitation of crystals by blending it along with a polyhydric alcohol fatty acid ester in the preparation. Furthermore, from Table 9, it was found that even if a patch having crystal precipitated by a long-time storage, the skin permeation rate of dexmedetomidine hydrochloride is not much influenced. Nevertheless, it is rather preferred that crystal precipitation is avoided in view of appearance of a preparation.

What is claimed is:

1. A hydrous adhesive patch, comprising:
   an adhesive gel base comprising dexmedetomidine or a salt thereof, a water-soluble polymer, a glycol, a fatty acid ester selected from the group consisting of a higher fatty acid alkyl ester, a polyhydric alcohol fatty acid ester, and a combination thereof, and water,
   wherein a content of the water in the adhesive gel base is 25 to 70 mass %.

2. The hydrous adhesive patch of claim 1, wherein a content of the water-soluble polymer in the adhesive gel base is 5 to 25 mass %.

3. The hydrous adhesive patch of claim 1, wherein the water-soluble polymer comprises a polyacrylic acid or a salt thereof and carboxymethylcellulose or a salt thereof.

4. The hydrous adhesive patch of claim 1, wherein the adhesive gel base has a pH of 6 to 7.

5. The hydrous adhesive patch of claim 1, wherein the glycol is propylene glycol.

6. The hydrous adhesive patch of claim 1, wherein the fatty acid ester is at least one of a C8-C24 fatty acid C1-C6 alkyl ester and a polyhydric alcohol C8-C24 fatty acid ester.

7. The hydrous adhesive patch of claim 1, wherein the fatty acid ester is at least one of isopropyl myristate and propylene glycol monocaprylate.

8. The hydrous adhesive patch of claim 1, wherein the fatty acid ester is C8-C24 fatty acid C1-C6 alkyl ester.

9. The hydrous adhesive patch of claim 1, wherein the fatty acid ester is isopropyl myristate.

10. The hydrous adhesive patch of claim 1, wherein a content of the glycol in the adhesive gel base is 10 to 60 mass %, and a content of the fatty acid ester in the adhesive gel base is 0.01 to 15 mass %.

11. The hydrous adhesive patch of claim 1, wherein the adhesive gel base is a sedative.

12. The hydrous adhesive patch of claim 2, wherein the water-soluble polymer comprises a polyacrylic acid or a salt thereof and carboxymethylcellulose or a salt thereof.

13. The hydrous adhesive patch of claim 2, wherein the adhesive gel base has a pH of 6 to 7.

14. The hydrous adhesive patch of claim 1, wherein the glycol is propylene glycol, and the fatty acid ester is at least one of a C8-C24 fatty acid C1-C6 alkyl ester and a polyhydric alcohol C8-C24 fatty acid ester.

15. The hydrous adhesive patch of claim 1, wherein the glycol is propylene glycol, and the fatty acid ester is at least one of isopropyl myristate and propylene glycol monocaprylate.

16. The hydrous adhesive patch of claim 1, wherein the glycol is propylene glycol, and the fatty acid ester is isopropyl myristate.

17. The hydrous adhesive patch of claim 15, wherein a content of the glycol in the adhesive gel base is 10 to 60 mass %, and a content of the fatty acid ester in the adhesive gel base is 0.01 to 15 mass %.

18. The hydrous adhesive patch of claim 16, wherein a content of the glycol in the adhesive gel base is 10 to 60 mass %, and a content of the fatty acid ester in the adhesive gel base is 0.01 to 15 mass %.

19. The hydrous adhesive patch of claim 1, further comprising:
   a backing layer on which the adhesive gel base is applied; and
   a covering film covering the adhesive gel base applied on the backing layer.

20. The hydrous adhesive patch of claim 1, wherein the fatty acid ester is a higher fatty acid alkyl ester.

21. The hydrous adhesive patch of claim 1, wherein the fatty acid ester comprises a higher fatty acid alkyl ester and a polyhydric alcohol fatty acid ester.

* * * * *